US 9,284,259 B2

(12) United States Patent  
Dutta et al.

(10) Patent No.: US 9,284,259 B2
(45) Date of Patent: Mar. 15, 2016

(54) PROCESS FOR REDUCING CHLORONITROBENZENE CATALYZED BY PLATINUM-NANOPARTICLES STABILIZED ON MODIFIED MONTMORILLONITE CLAY

(71) Applicant: Council of Scientific & Industrial Research, New Delhi (IN)

(72) Inventors: Dipak Kumar Dutta, Jorhat (IN); Dipanka Dutta, Jorhat (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/550,373

(22) Filed: Nov. 21, 2014

(65) Prior Publication Data  
US 2015/0080609 A1 Mar. 19, 2015

Related U.S. Application Data

(63) Continuation of application No. PCT/IN2013/000698, filed on Nov. 18, 2013.

(30) Foreign Application Priority Data

Jul. 23, 2013 (IN) .............................. 2183/DEL/2013

(51) Int. Cl.  
C07C 209/00 (2006.01)  
C07C 209/36 (2006.01)  
(Continued)

(52) U.S. Cl.  
CPC ............. *C07C 209/365* (2013.01); *B01J 23/42* (2013.01); *B01J 29/043* (2013.01); *B01J 35/006* (2013.01);  
(Continued)

(58) Field of Classification Search  
CPC combination set(s) only.  
See application file for complete search history.

(56) References Cited

U.S. PATENT DOCUMENTS 4,070,401 A 1/1978 Hirai et al.  
4,375,550 A 3/1983 Bird et al.  
(Continued)

FOREIGN PATENT DOCUMENTS

CN 101745382 6/2010

OTHER PUBLICATIONS

Greenfield et al., "Metal Sulfide Catalysts for Hydrogenation of Halonitrobenzenes to Haloanilines" J. Organic Chem., May 5, 1967, vol. 32, pp. 3670-3671.

(Continued)

*Primary Examiner* — Clinton Brooks  
(74) *Attorney, Agent, or Firm* — Brinks Gilson & Lione

(57) ABSTRACT

$Pt^0$-nanoparticles in the size range of 0 to 10 nm were prepared in-situ by impregnation of $H_2PtCl_6.6H_2O$ into the nanopores of modified montmorillonite followed by reduction with different reducing agents like ethylene glycol, sodium citrate, hydrogen, hydrazine and sodium borohydrate. The montmorillonite was modified by activation with mineral acids under controlled condition for generating desired nanopores. XRD pattern of $Pt^0$-nanoparticles revealed the formation of face centered cubic (fcc) lattice. These supported $Pt^0$-nanoparticles show efficient catalytic activity for the selective reduction of chloronitrobenzenes. As a typical example, at a $H_2$ pressure of 10 bars, temperature 45° C. for a period of 15 min, the $Pt^0$-nanoparticles (prepared by reduction with hydrazine) exhibit conversion of o-chloronitrobenzene up to 100% and selectivity >99% to o-chloroanilines with very negligible amount of C—Cl bond cleavage.

5 Claims, 1 Drawing Sheet

(51) Int. Cl.
- *B01J 23/42* (2006.01)
- *B01J 37/02* (2006.01)
- *B01J 37/06* (2006.01)
- *B01J 37/16* (2006.01)
- *B01J 29/04* (2006.01)
- *B01J 35/00* (2006.01)
- *B01J 35/10* (2006.01)

(52) U.S. Cl.
CPC .......... *B01J 35/0013* (2013.01); *B01J 35/1019* (2013.01); *B01J 35/1038* (2013.01); *B01J 35/1061* (2013.01); *B01J 37/0203* (2013.01); *B01J 37/0236* (2013.01); *B01J 37/06* (2013.01); *B01J 37/16* (2013.01); *B01J 2229/186* (2013.01); *B01J 2229/37* (2013.01)

(56) References Cited

U.S. PATENT DOCUMENTS

| | | |
|---|---|---|
| 4,760,187 A | 7/1988 | Kosak |
| 5,068,436 A | 11/1991 | May |
| 5,105,011 A | 4/1992 | Cordier et al. |
| 5,126,485 A | 6/1992 | Bailliard et al. |
| 7,288,500 B2 | 10/2007 | Liu et al. |
| 7,381,844 B2 | 6/2008 | Liu et al. |

OTHER PUBLICATIONS

F. Wang et al., "Layered material γ-ZrP supported platinum catalyst for liquid-phase reaction: a highly active and selective catalyst for hydrogenation of the nitro group in *para*-chloronitrobenzene", Chem. Commun., (2008), pp. 2040-2042.

Zhang et al., "Magnetic nanocomposite catalysts with high activity and selectivitiy for selective hydrogenation of *ortho*-chloronitrobenzene", Journal of Catalysis, 229, (2005), pp. 114-118.

Chang et al., Polyethylene glycol-stabilized platinum nanoparticles: The efficient and recyclable catalysts for selective hydrogenation of *o*-chloronitrobenzene to *o*-chloroaniline, Journal of Colloid & Interface Science, 336, (2009), pp. 675-678.

Xiao et al., "Ionic-liquid-like copolymer stabilized nanocatalysts in ionic liquids I. Platinum catalyzed selective hydrogenation of *o*-chloronitrobenzene", Journal of Catalysis, 250 (2007), pp. 25-32.

Corma et al., "Transforming Nonselective into Chemoselective Metal Catalysts for the Hydrogenation of Substituted Nitroaromatics", Journal of the American Chemical Society, 130 (2008), pp. 8748-8753.

Liu et al., "Shape-Controlled Synthesis and Catalytic Behavior of Supported Platinum Nanoparticles", Synlett, (2009), No. 4, pp. 595-598.

Motoyama et al., "Catalysis in Polysiloxane Gels: Platinum-Catalyzed Hydrosilylation of Polymethylhydrosiloxane Leading to Reusable Catalysts for Reduction of Nitroarenes", Organic Letters, (2009), vol. 11, No. 6, pp. 1345-1348.

Dutta et al., "Synthesis and catalytic activity of Ni°-acid activated montmorillonite nanoparticles", Applied Clay Science, 53 (2011), pp. 650-656.

International Search Report and Written Opinion of International Application No. PCT/IN2013/000698 dated Mar. 4, 2014; 10 pages.

Parida et al.; "Schiff Base Pt(II) Complex Intercalated Montmorillonite: A Robust Catalyst for Hydrogenation of Aromatic Nitro Compounds at Room Temperature", Industrial & Engineering Chemistry Research, (2011), vol. 50, No. 13, pp. 7849-7856.

Pan et al.; "Preparation of Platinum/Montmorillonite Nanocomposites in Supercritical Methanol and Their Application in the Hydrogenation of Nitrobenzene", Catalysis Letters, Kluwer Academic Publishers-Plenum Publishers, NE, vol. 131, No. 1-2, May 22, 2009, pp. 179-183.

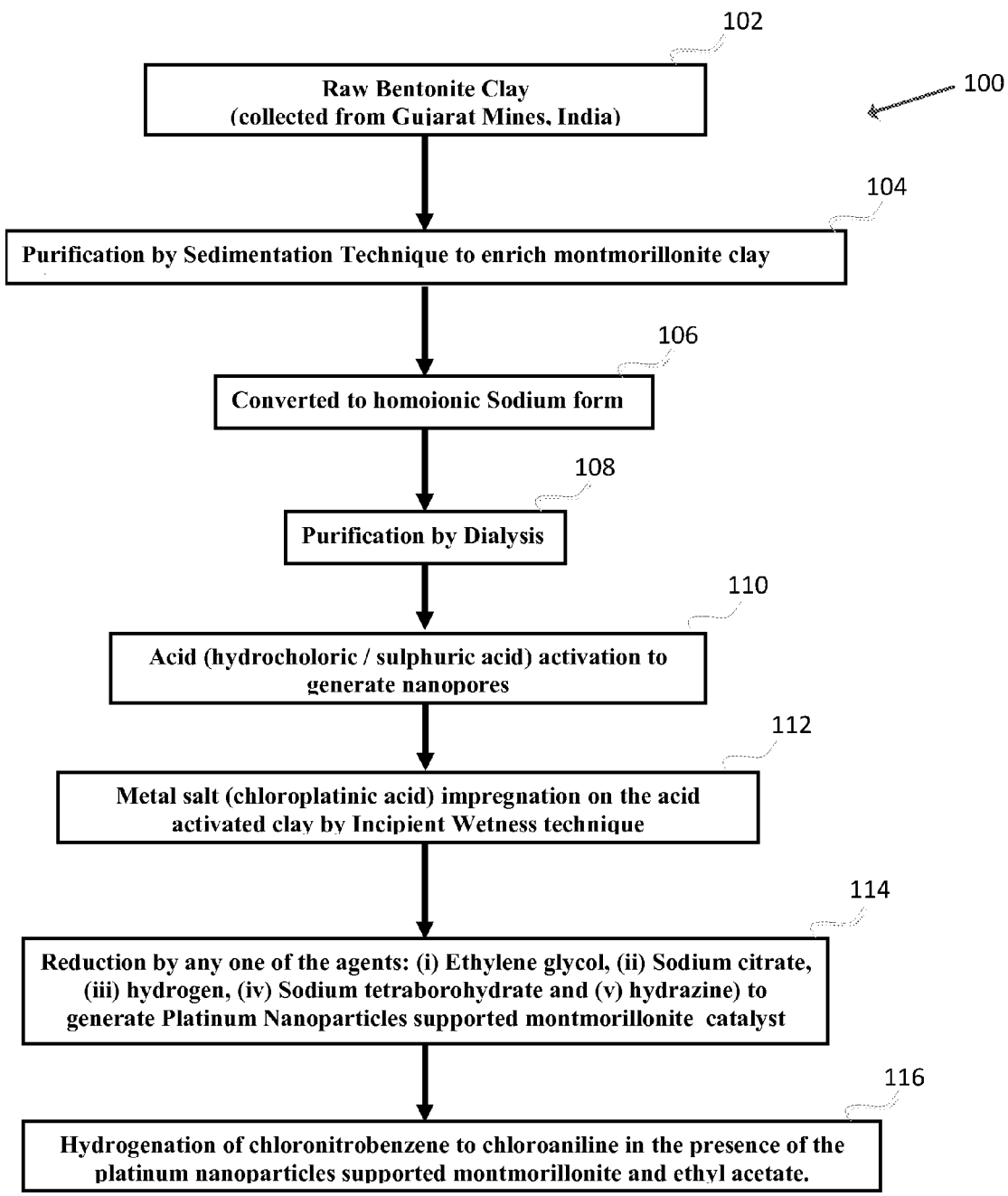

PROCESS FOR REDUCING CHLORONITROBENZENE CATALYZED BY PLATINUM-NANOPARTICLES STABILIZED ON MODIFIED MONTMORILLONITE CLAY

CROSS REFERENCE TO RELATED APPLICATIONS

This application is a continuation-in-part of Patent Cooperation Treaty (PCT) International Application Serial No. PCT/IN2013/000698, filed on Nov. 18, 2013, and which designates the Unites States and claims priority under 35 U.S.C. §119 to Indian Application Serial No. 2183/DEL/2013, filed on Jul. 23, 2013. The entirety of both Patent Cooperation Treaty (PCT) International Application Serial No. PCT/IN2013/000698 and Indian Application Serial No. 2183/DEL/2013 are hereby incorporated by reference herein.

FIELD OF THE INVENTION

The embodiments of the present invention relate to a process for reducing chloronitrobenzene catalyzed by platinum-nanoparticles stabilized on modified montmorillonite clay. More particularly, the embodiments of the present invention relate to the preparation of $Pt^0$-nanoparticles supported on modified montmorillonite clay, where the modification of the clay was carried out by activating with mineral acids such as HCl under controlled conditions in order to generate nanopores in the range 0 to 8 nm for in-situ synthesis of $Pt^0$ nanoparticle. The embodiments of the present invention still more particularly relate to an improved process for the selective reduction of chloronitrobenzenes to the corresponding chloroanilines catalyzed by the environmentally benign and recyclable $Pt^0$-nanoparticles supported on modified montmorillonite clay

BACKGROUND

Aromatic haloamines are an important class of industrial intermediates for the synthesis of organic fine chemicals, such as dyes, drugs, herbicides and pesticides. The main routes of synthesis of the haloamines involved reduction of corresponding nitrocompounds catalysed by either metal-acid systems or with noble metal. Processes involving later route are favored now a days due to environmental issues associated with the use of hydrochloric acid in the former route.

Control of selectivity is the critical problem while carrying out hydrogenation of halonitroaromatics with noble metals. Apart from the formation of alogenated aromatic amines, extensive dehalogention by cleaving the carbon-halogen bond also occurs. In addition, by-products such as azo and azoxyhalobenzenes are also formed. Furthermore, hydrogen chloride which is produced by the dehalogenation reaction greatly contributes to the corrosion of the reactor.

Attempts were done to minimize the side reaction by the addition of selectivity promoters or dehalogenated inhibitor such as bases or other electron donating compounds along with noble metal catalyst. Numerous efforts (Greenfield et. al. J. Organic Chem., 1967, Vol. 32, Page 3670-3671) are being done to suppress the dehalogenation reaction and to minimize other by-products, including a method of using sulfides of noble metal as a catalyst and a method of adding dehalogenation inhibitor. Disadvantages of using noble metal sulphides are low catalytic activity and complicated preparation processes of these catalysts.

In U.S. Pat. No. 4,070,401, Hirai and Miyata describe a method for the preparation of a halogenated aromatic amine, wherein, a halogenated aromatic nitro compound is hydrogenated in liquid phase in the presence of a platinum-base catalyst to obtain a corresponding halogenated aromatic amine. The hydrogenation is carried out in the presence of an alkylmonoamine, an alicylic amine or a polyalkylenepolyamine The main drawback of the process is that it takes a longer reaction time, i.e. 40 to 210 minutes, depending upon the substrates and a pressure of about 50 kg/cm$^2$, although the conversion was 88.7 to 98.5%.

Reference may be made to U.S. Pat. No. 4,375,550, wherein the hydrogenation of halogen-substituted aromatic nitro compounds to corresponding amino compounds were carried out at elevated temperature (50-200° C.) and pressure (1-70 atm) using catalysts consisted of platinum, palladium, rhodium, iridium, ruthenium and osmium supported on carbon material. The main drawback of the process is that it involves precious metals as well as the drastic process parameters.

In U.S. Pat. No. 4,760,187, Kosak discloses a process of reducing chloro-nitrobenzenes to corresponding chloroanilines catalysed by metallic ruthenium-platinum at a pressure of 200 to 800 psi and temperature 70 to 160° C. The products generated is contaminated with by-products. Further, prolonged reaction time is required for an economical degree of conversion.

Reference may be made to U.S. Pat. No. 5,068,436, wherein, a process of reducing fluorinated or chloro-nitrobenzenes to corresponding haloanilines in presence of noble metals (such as rhodium, palladium, iridium, and platinum) supported on carbon/Raney nickel or cobalt catalyst in acidic catalytic medium is described. The process is associated with pressure (hydrogen) in the range 50 to 2000 psi, temperature 50 to 100° C., time of reaction 1 to 2 h to yield greater than 99%. The isolated yield is 80 to 90%. The main drawback of the process was that it involved precious metals, complicated process parameters, higher reaction time and lower isolated yields.

Reference may be made to U.S. Pat. No. 5,105,011, wherein, a process is described for hydrogenation of halogenonitroaromatic compounds in the presence of a nickel-, cobalt- or iron-based catalyst preferably by Raney nickel and hydrogen in the presence of iodine at a temperature from 50 to 150° C. and preferable pressure 1 to 100 bar. The main drawback of the process is that it involves some cumbersome steps, high pressure and a mixture of products were obtained.

Reference may be made to U.S. Pat. No. 5,126,485, wherein, a process is described for hydrogenation of halogenonitroaromatic compounds in the presence of a nickel-, cobalt- or iron-based catalyst preferably by Raney nickel and hydrogen in the presence of a sulfur-containing compound like sulfoxide or sulfone, at a temperature from 50 to 150° C. and preferable pressure 1 to 100 bar. The main drawback of the process is that it is associated with some cumbersome steps, high pressure and a mixture of products were obtained.

In U.S. Pat. No. 7,288,500 B2, Liu et al., describes a process wherein, hydrogenation of halonitroaromatic compounds is carried out in the presence of supported (carbon black, activated carbon, silica, alumina etc.) metals (palladium, platinum, ruthenium and rhodium) complexes of acetylacetone backbone ligands followed by reduction at temperature less than 160° C. The catalytic reduction is carried out at temperature 0 to 160° C., pressure 1 to 100 bar and reaction time 10.25 to 13.5 h to yield mixtures of compounds (selectivity 76 to 97%). The main drawback of the process is that the process involves several complex steps of catalysts preparation and yields were impure products.

Reference may be made to U.S. Pat. No. 7,381,844, wherein, a process is described for hydrogenation of chlorinatednitrobenzene at temperature 40 to 150° C. and pressure 5 to 40 atm in the presence of nanosized boron-containing nickel catalyst within a reaction time 10 to 80 minutes to give conversion 20 to 100% and selectivity higher than 99%. The main drawback of the process is that the process involves several complex steps of catalysts preparation and higher reaction time to yield higher selectivity. The aforementioned U.S. patents are hereby incorporated by reference herein.

Chinese Patent No. CN101745382, discloses a catalyst for synthesizing parachloroaniline from parachloronitrobenzene by hydrogenation and a preparation method thereof. The active component of the catalyst is Pt, the carrier is attapulgite, and the content of the Pt is in the range of 0.1 wt % to 5 wt %. The catalyst not only has high activity, but also effectively inhibits the generation of a dechlorination reaction. Under the condition that the parachloronitrobenzene is completely transformed, the selectivity of 100% for the parachloroaniline is realized. The attapulgite clay with a mineral acid acidified (sulfuric acid or hydrochloric acid) to a concentration of 2-10 wt %. Polyvinyl pyrrolidone and chloroplatinic acid-treated attapulgite were obtained after the acid solution was stirred at room temperature and dried to obtain a catalyst precursor. Finally, the catalyst precursor in a stream of hydrogen at 200~500° C. reduction of 2 to 10 h was used to obtain a catalyst by filtration, washing and drying procedure. The invention does not disclose the particle size of the Pt catalyst nor the surface area of the modified attapulgite matrix after acid modification. The overall process of the invention is cumbersome and lengthy. Chinese Patent No. CN101745382 is hereby incorporated by reference herein.

Reference may be made to F. Wang et. al. Chem. Commun, (2008) 2040-2042, wherein, liquid phase hydrogenation of p-chloronitrobenzene in methanol is carried out at 40° C., $H_2$ pressure in the range 20-40 bar and time of reaction from 20 to 275 minutes in presence of polyvinylpyrrolidone protected platinum nanoparticles supported on layered zirconium phosphate in order to obtain conversion 74 to 100% and selectivity 94 to 100%. The main drawback of the above process is that it involves higher pressure and longer reaction time.

Zhang et. al. reports (J. Catalysis, 229, 2005, 114-118) that use of $Pt/\gamma$-$Fe_2O_3$ catalyst results in about 100% conversion of o-chloronitrobenzene to o-chloroaniline within 10 to 392 min with conversion 49 to 100% and selectivity 45 to 99.9%. The reaction was carried out in methanol at a temperature 60° C. and pressure 10 to 40 bar. The main drawback of the process is that it involves considerably high pressure.

Reference may be made to Chang et. al., J. Colloid & In. Sc. 336 (2009) 675-678, wherein it reports that platinum nanoparticles, immobilized in PEGs, catalyze hydrogenation of o-chloronitrobenzene with conversion 31 to 100%, selectivity 84 to 99.7%, within a reaction time from 30 to 600 min, temperature 40 to 80° C., and pressure 10 to 50 bar. The conversion and selectivity were lowered by the aggregation of Pt particles because the amount of PEG is not enough to protect platinum nanoparticles. Another drawback of the process is that the separation of catalyst from the reaction mixture is not simple.

Xiao et. al. reports (J. Catalysis, 250, 2007, 25-32) that use of platinum nanoparticles stabilized by ionic liquid like copolymer catalyst results in 77.5% to 95.9% conversion of o-chloronitrobenzene to o-choloroaniline and 95.1% to 99.9% selectivity within a period from 0.83 to 1 h. The reaction is carried out at a temperature of 60° C. and 40 bar $H_2$ pressure. The main drawback of the process is that it involves high pressure.

Reference may be made to Corma et. al. (J. Am. Chem. Soc. 130, 2008, 8748-8753), wherein hydrogenation of substituted nitroaromatics are carried by using platinum nanoparticles supported by $TiO_2$ in tetrahydrofuran (THF) with 95% selectivity within a period of 0.35 to 6.5 h. The reaction is carried out at temperature 45° C. and 3 to 6 bar $h_2$ pressure. The main drawback of the process is that it takes high time for the complete conversion.

Reference may be made to Liu et. al. (Synlett, 2009, 595-598) wherein, hydrogenation of o-chloronitrobenzene is carried out by using platinum nanoparticles supported carbon catalyst in ethanol with 100% conversion and 66.5 to 99.4% selectivity. The reaction is carried out at 25° C. and 10 bar $H_2$ pressure within 4.5 to 10 h. The main drawback is that the process is time consuming and selectivity is low.

Reference may be made to Motoyama et. al. (Organic Lett., 11, 2009, 1345-1348), wherein, the hydrogenation of m-chloronitrobenzene and o-chloronitrobenzene is carried out by polysiloxane gel encapsulated platinum nanoparticles in ethyl acetate with conversion in the range 63 to 99%. The reaction is carried out at 25° C., 10 atm $H_2$ pressure and for 24 h. The main drawback of the process is that it requires a long time for the reaction.

Reference may be made to Dutta et al. (Synthesis and catalytic activity of $Ni^o$-acid activated montmorillonite nanoparticles, Applied Clay Science 53, 2011, 650-656), wherein, the montmorillonite clay is modified by acid activation with mineral acid under controlled condition for generating nanoporous materials for using as support for $Ni^o$-nanoparticles. The supported $Ni^o$-nanoparticles showed efficient activity in transfer hydrogenation of acetophenone to 1-phenylethanol with high very efficiency. The aforementioned journal articles are hereby incorporated by reference herein.

SUMMARY

A process for reducing chloronitrobenzene catalyzed by platinum-nanoparticles stabilized on modified montmorillonite clay wherein the said process comprises the steps of dissolving chloronitrobenzene in ethyl acetate in the mole ratio of 1:50 to obtain a solution; adding $Pt^0$-nanoparticles stabilized on modified montmorillonite as catalyst in the mole ratio of 1:82 with respect to chloronitrobenzene to the solution obtained in step a to obtain a reaction mixture; purging $H_2$ gas for 5 min in the reaction mixture obtained in step b and then pressurizing with $H_2$ gas with a pressure in the range of 5 bar to 20 bar at room temperature; and heating the reaction mixture as obtained in step c to a temperature in the range of 40° C. to 50° C. for a period of reaction in the range of 5 minutes to 240 minutes at 500 rpm to obtain chloroaniline.

In another embodiment of the invention, modifying of the Na-montmorillonite was carried out with mineral acid (such as hCl) treatment and activating at about 80° C. for 1 h in order to achieve desired pore size in the range 0-8 nm with an average pore diameter of about 4 nm and high surface area 578.5 $m^2$/g.

BRIEF DESCRIPTION OF THE DRAWINGS

FIG. 1 is a process flow diagram that shows the different major steps that are involved in the preparation of $Pt^0$-Nanoparticles-montmorillonite clay composites and their catalytic application in hydrogenation of chloronitrobenzene to chloroaniline, according to an embodiment of the present invention.

DETAILED DESCRIPTION

The embodiments of the present invention provide a process for reducing chloronitrobenzene catalyzed by Platinum-nanoparticles stabilized on modified montmorillonite clay which comprises contacting gaseous hydrogen with liquid reaction composition containing chloronitrobenzene and ethylacetate at a temperature around 45° C. and at a pressure in the range of 5 bar to 20 bar for a periods of 5 min to 240 min in the presence of $Pt^0$-nanoparticles catalyst prepared by successful loading of $H_2PtCl_6.6H_2O$ metal precursor into the nanopores of modified montmorillonite clay by incipient wetness impregnation technique followed by reduction using different reducing agents.

One of the objectives of embodiments of the present invention is to provide a process for reducing chloronitrobenzene catalyzed by platinum-nanoparticles stabilized on modified montmorillonite clay, which obviates the drawbacks of the hitherto known prior arts.

Another objective of embodiments of the present invention is to provide a process for preparation of chloroanilines from respective chloronitrobenzenes without cleaving of C—Cl bond giving about 100% selectivity and leading to 100% conversion within a minimum reaction time.

Another objective of embodiments of the present invention is the generation of $Pt^0$-nanoparticles into the nanopores of the modified montmorillonite support by loading of $H_2PtCl_6.6H_2O$ metal precursor followed by reduction with different reducing agents such as $NaBH_4$, ethylene glycol, hydrazine, etc. under standard technique.

Still another object of embodiments of the present invention is to provide a clean, consistently recyclable and robust catalyst for selective reduction of chloronitrobenzenes to the corresponding chloroanilines at comparatively lower pressure and lesser time.

In one embodiment of the present invention, the selectivity to chloroanilines is higher than 99% and conversion up to 100%.

In another embodiment of the present invention, the modification of the Na-montmorillonite was carried out with mineral acid (such as HCl) treatment and activating at about 80° C. for 1 h in order to achieve desired pore size in the range of 0 nm to 8 nm with an average pore diameter of about 4 nm and high surface area 578.5 $m^2/g$.

In another embodiment of the present invention, the platinum nanoparticles were prepared by impregnation of $H_2PtCl_6.6H_2O$ metal salt into the nanopores of modified montmorillonite clay by incipient wetness impregnation technique under vigorous stirring condition. The stirring was continued for 6 h followed by evaporation to dryness in a rotary evaporator. The dry clay-$H_2PtCl_6$ composite was dispersed in 50 ml ethylene glycol in a round bottom flask and was refluxed at 196° C. for 6 h under stirring condition. The products were recovered, washed with methanol until free from ethylene glycol and then dried at about 40° C. for 12 h.

In yet another embodiment of the present invention, $Pt^0$-nanoparticles stabilized on modified montmorillonite as catalyst is added in the mole ratio of 1:82 with respect to chloronitrobenzene.

In another embodiment of the present invention, hydrogenation reaction was carried out at a pressure in the range of 5 bar to 20 bar.

In another embodiment of present invention, wherein organic solvent used in hydrogenation reaction was ethyl acetate.

In one embodiment of the present invention, the catalytic reaction was carried out in a 50 ml autoclave equipped with temperature and pressure control. A typical hydrogenation reaction was carried out by dissolving 1 mmol (157.5 mg) of chloronitrobenzene in ethyl acetate (5 ml) together with 16 mg of catalyst containing $Pt^0$-nanoparticles supported on modified montmorillonite clay and the reaction vessel was purged with $H_2$ gas for about 5 min and then pressurized with $H_2$ gas up to 5 bar to 20 bar at room temperature (25° C.). The temperature of the reactor was raised to 45±5° C. The reaction was allowed for 5 min-240 min and the reaction mixtures were collected, the insoluble catalysts were recovered by simple filtration technique, and the product was determined by gas chromatography.

In an embodiment of the present invention, a process of purification of the montmorillonite clay has been described as: about 60 g of montmorillonite clay (M/S Gujarat Mines Bentonite, Gujarat) exhibiting cation exchange capacity (CEC) 126 meq/100 g of clay determined by standard technique and evaluated by XRD as: Oriented films for the study were prepared from Na-montmorillonite on glass slides by allowing a few drops of suspension of the clay in water and then dried at room temperature. The basal spacings ($d_{001}$) at room temperature as determined by XRD technique were found to be around 12.5 Å. The slide was kept over ethylene glycol in a closed desiccator for about 24 h and the basal spacing ($d_{001}$) was found to be 16.5 Å. Montmorillonite clay mineral was added under constant stirring to about 3000 ml distilled water in 5000 ml beaker and allowed to settle for about 20 h and the slurry collected from 18 cm from the top of the surface in order to collect less than 2 μm fraction particle size. The collected clay was dried at 50±5° C. in air oven to get solid mass.

In another embodiment of the present invention, a process for conversion into Na-montmorillonite has been described as: about 2 g of dry purified montmorillonite clay was suspended in 100 ml of distilled water and to it 100 ml of 2M NaCl solution was added and kept stirring for about 2 h. The mass was allowed to settle and supernatant liquid was decanted off. The slurry was again treated with 2M NaCl solution and stirred. This step was repeated for about four times. The excess NaCl was removed by dialyzing the residue against distilled water till the conductivity of dialyzed approached that of distilled water and showed negative test for chloride ion with silver nitrate. The mass was then dried at 50±5° C. in air oven.

In another embodiment of the present invention, a process for preparation of acid activated montmorillonite has been described in order to prepare micro-(<2 nm) and mesoporous (2-50 nm) aluminosilicates from montmorillonite clay minerals containing mainly octahedral and tetrahedral aluminium in the framework. The process comprises mixing the clay mineral with desired acid to leach substantially the octrahedral aluminium while leaving preferably the tetrahedral aluminium. The process has been described as: in a round bottom flask, 5 g of montmorillonite clay was taken and to it 100 ml of 4M HCl was added. The resulting dispersion was refluxed at about 100° C. for a period of 1 h. After cooling down the mixture to room temperature, the slurry was filtered through Whatman 41 filter paper and the residue was washed with distilled water till it becomes acid free. The clay was then dried in air oven at 50±5° C. over night to obtain the solid product. The yield was 90.2%.

In still another embodiment of the present invention, a process has been described for preparation of porous materials with high surface area (BET) up to 578.5 m²/g, pore volume 0.5965 cc/g and a pore diameter in the range of 0 nm to 8 nm with an average pore diameter of 4.12 nm from montmorillonite clay by acid activation in order to use as solid support for generation of Pt⁰-nanoparticles.

The embodiments of the present invention also provide a method of generation of Pt⁰-nanoparticles as follows: 0.5 g of acid treated clay were taken in 100 ml round bottom flask to which 32 ml (0.02 M) aqueous solution of $H_2PtCl_6.6H_2O$ were added slowly under vigorous stirring condition. The stirring was continued for another 10-12 h followed by evaporation to dryness in rotary evaporator. The dry clay-$H_2PtCl_6$ composite were reduced with $NaBH_4$ or Ethylene glycol or Sodium Citrate or hydrazine or molecular hydrogen by adopting standard methods. The products were recovered, washed and then dried at about 40° C. for 12 h.

The size and morphology of Pt⁰-nanoparticles were characterized by TEM. It is evident from the TEM images that the average size distributions of Pt⁰-nanoparticles are in the range of 0 nm to 10 nm. The micrographs clearly indicate that the particles have a spherical morphology and well dispersed on the support. Selected Area Electron Diffraction (SAED) pattern revealed the formation of hexagonal symmetry diffraction spot pattern indicating Pt⁰-nanoparticles were single crystalline in nature. The crystalline natures of the Pt⁰-nanoparticles were confirmed by the corresponding powder XRD pattern. The four sharp peaks of 2θ value 39.9 degrees, 46.5 degrees, 68.3 degrees, and 81.5 degrees can be assigned to the (111), (200), (220) and (311) indices of face centered cubic (fcc) lattice of Platinum. The average particle size of the Pt⁰-nanoparticles prepared by using different reducing agents were calculated by using Scherrer equation and are given in Table 1. In order to ascertain the oxidation state, the samples were characterized by XPS analysis. The XPS spectra of Pt⁰-nanoparticles with two peak of binding energy 71.3 ev and 74.6 ev corresponding to Pt $4f_{7/2}$ and $4f_{5/2}$ levels confirm the presence of platinum in metallic state (zero oxidation state).

TABLE 1

Surface Characterization of samples & Average Particle size calculated from Scherrer equation:

| Samples | Surface Area (m²/g) | Pore Diameter (nm) | Pore Volume (cc/g) | Average Size (nm) |
|---|---|---|---|---|
| 4M HCl 1H AT-GMB | 578.5 | 4.12 | 0.5965 | — |
| $H_2PtCl_6$-AT-GMB | 49.59 | 6.94 | 0.0861 | — |
| Pt⁰- reduced by Sodium Citrate | 325.33 | 5.05 | 0.4110 | 4.1 |
| Pt⁰- reduced by Polyol | 262.86 | 4.98 | 0.3277 | 8.2 |
| Pt⁰- reduced by $H_2$ | 224.24 | 4.34 | 0.2438 | 9.2 |
| Pt⁰- reduced by $NaBH_4$ | 159.95 | 5.70 | 0.2279 | 7.5 |
| Pt⁰- reduced by hydrazine | 160.77 | 4.99 | 0.2006 | 8.7 |

FIG. 1 is a process flow diagram that shows the different major steps that are involved according to an embodiment of the present invention. Process 100 illustrates the preparation of Pt⁰-Nanoparticles-montmorillonite clay composites and their catalytic application in hydrogenation of chloronitrobenzene to chloroaniline. Raw bentonite clay is collected from Gujarat Mines, India (step 102). Then, the raw bentonite clay is purified by a sedimentation technique to enrich montmorillonite clay (step 104). The enriched montmorillonite clay is then converted to a homoionic sodium form (step 106), followed by purification by dialysis (step 108). Following purification by dialysis, acid (hydrochloric/sulphuric acid) activation of the clay is used to generate nanopores (step 110). Then, an incipient wetness technique is carried out for the purposes of metal salt (chloroplatinic acid) impregnation on the acid activated clay (step 112). Following step 112, platinum nanoparticles supported montmorillonite catalysts are generated by carrying out reduction with any one of the following agents: (i) ethylene glycol; (2) sodium citrate; (iii) hydrogen; (iv) sodium tetraborohydrate; and (v) hydrazine (step 114). Finally, hydrogenation of chloronitrobenzene to chloroaniline is carried out in the presence of the platinum nanoparticles supported montmorillonite and ethyl acetate (step 116).

EXAMPLES

The following examples are given by the way of illustration of the working of the embodiments of the present invention in actual practice and therefore should not be constructed to limit the scope of the embodiments of the present invention.

Example 1

0.5 g of acid activated montmorillonite was taken in 100 ml round bottom flask and 32 ml (0.02 M) aqueous solution of $H_2PtCl_6.6H_2O$ was added slowly under vigorous stirring condition. The stirring was continued for another 10 h followed by evaporation to dryness in a rotary evaporator. The dry clay-$H_2PtCl_6$ composite was dispersed in 50 ml ethylene glycol in a double necked round bottom flask and was refluxed at 196° C. for 6 h in nitrogen environment under stirring condition. The products were recovered, washed with methanol until free from ethylene glycol and then dried at about 40° C. for 12 h. The yield was about 90%. The resultant Pe-nanoparticles exhibit surface area 262.86 m²/g, specific pore volume 0.3277 cc/g and average pore diameter 4.98 nm.

Example 2

0.5 g of acid activated montmorillonite was taken in 100 ml round bottom flask and 32 ml (0.02 M) aqueous solution of $H_2PtCl_6.6H_2O$ was added slowly under vigorous stirring condition. The stirring was continued for another 10 h followed by evaporation to dryness in a rotary evaporator. The dry clay-$H_2PtCl_6$ composite was dispersed in 10 ml water and 0.38 mg $NaBH_4$ (1 M) in 10 ml distilled water was added slowly over 15 min under constant stirring and the color was changed immediately from yellow to black. The mass was allowed to settle and washed with distilled water several times until the content was free of chloride ions and then dried at about 40° C. for 12 h. The yield was about 92%. The resultant Pt⁰-nanoparticles exhibit surface area 159.95 m²/g, specific pore volume 0.2279 cc/g and average pore diameter 5.70 nm.

Example 3

0.5 g of acid activated montmorillonite was taken in 100 ml round bottom flask and 32 ml (0.02 M) aqueous solution of $H_2PtCl_6.6H_2O$ was added slowly under vigorous stirring condition. The stirring was continued for another 10 h followed by evaporation to dryness in a rotary evaporator. The dry clay-$H_2PtCl_6$ composite was dispersed in 10 ml water and 2.58 mg sodium citrate (1 M) in 10 ml distilled water was added and refluxed at 80° C. for 2 h under constant stirring. The resultant mass was allowed to settle and washed with distilled water several times and then dried at about 40° C. for 12 h. The yield was about 95%. The resultant $Pt^0$-nanoparticles exhibit surface area 325.33 $m^2$/g, specific pore volume 0.4110 cc/g and average pore diameter 5.05 nm.

Example 4

0.5 g of acid activated montmorillonite was taken in 100 ml round bottom flask and 32 ml (0.02 M) aqueous solution of $H_2PtCl_6.6H_2O$ was added slowly under vigorous stirring condition. The stirring was continued for another 10 h followed by evaporation to dryness in a rotary evaporator. The dry clay-$H_2PtCl_6$ composite was dispersed in 10 ml water and 0.32 ml hydrazine (1 M) in 10 ml distilled water was added and stirred for 1 h under room temperature. The resultant mass was allowed to settle and washed with distilled water several times and then dried at about 40° C. for 12 h. The yield was about 92%. The resultant $Pt^0$-nanoparticles exhibit surface area 160.77 $m^2$/g, specific pore volume 0.2006 cc/g and average pore diameter 4.99 nm.

Example 5

0.5 g of acid activated montmorillonite was taken in 100 ml round bottom flask and 32 ml (0.02 M) aqueous solution of $H_2PtCl_6.6H_2O$ was added slowly under vigorous stirring condition. The stirring was continued for another 10 h followed by evaporation to dryness in a rotary evaporator. The dry clay-$H_2PtCl_6$ composite was dispersed in 20 ml water in a 50 ml round bottom flask and $H_2$ gas was introduced into the mixture through a balloon and the reaction mixture was kept under constant stirring. The resultant mass was allowed to settle and washed with distilled water several times and then dried at about 40° C. for 12 h. The yield was about 96%. The resultant $Pt^0$-nanoparticles exhibit surface area 224.24 $m^2$/g, specific pore volume 0.2438 cc/g and average pore diameter 4.34 nm.

Example 6

1 mmol (157.5 mg) of p-chloronitrobenzene was dissolved in ethyl acetate (5 ml) and 16 mg of catalyst containing $Pt^0$-nanoparticles supported on modified montmorillonite clay reduced by $NaBH_4$ was added in a 50 ml hastelloy autoclave equipped with temperature and pressure control. The reaction vessel was purged with $H_2$ gas for about 5 min and then pressurized with $H_2$ gas up to 5 bar at room temperature (25° C.). The reaction was carried out at temperature 50° C. for a period of 240 min at 500 rpm. After the catalytic reaction, the reaction mixtures were collected, the insoluble catalysts were recovered by simple filtration technique, and the product was determined by gas chromatography. GC analysis showed conversion was about 43% and selectivity of the p-chloroaniline was 100%.

Example 7

1 mmol (157.5 mg) of p-chloronitrobenzene was dissolved in ethyl acetate (5 ml) and 16 mg of catalyst containing $Pt^0$-nanoparticles supported on modified montmorillonite clay reduced by $NaBH_4$ was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 5 min at 500 rpm. After the catalytic reaction, the reaction mixtures were collected, the insoluble catalyst was recovered by simple filtration technique, and the product was determined by gas chromatography. GC analysis showed conversion was about 74.6% and selectivity of the p-chloroaniline was 97.7%.

Example 8

17 mmol (157.5 mg) of p-chloronitrobenzene was dissolved in ethyl acetate (5 ml) and 16 mg of catalyst containing $Pt^0$-nanoparticles supported on modified montmorillonite clay reduced by $NaBH_4$ was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 40° C. for a period of 10 min at 500 rpm. After the catalytic reaction, the reaction mixtures were collected, the insoluble catalyst was recovered by simple filtration technique, and the product was determined by gas chromatography. GC analysis showed conversion was about 94.3% and selectivity of the p-chloroaniline was 97.1%.

Example 9

1 mmol (157.5 mg) of chloronitrobenzene (ortho and para) was dissolved in ethyl acetate (5 ml) and 16 mg of catalyst containing $Pt^0$-nanoparticles supported on modified montmorillonite clay reduced by $NaBH_4$ was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 15 min at 500 rpm. After the catalytic reaction, the reaction mixture was collected, the insoluble catalyst was recovered by simple filtration technique, and the product was determined by gas chromatography. GC analysis showed conversion of o-chlorobenzene was about 99.8% and selectivity of the o-chloroaniline was 99.6% and conversion of p-chlorobenzene was about 98.3% and selectivity of the p-chloroaniline was 99.0%.

Example 10

1 mmol (157.5 mg) of m-chloronitrobenzene was dissolved in ethyl acetate (5 ml) and 16 mg of catalyst containing $Pt^0$-nanoparticles supported on modified montmorillonite clay reduced by $NaBH_4$ was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 30 min at 500 rpm. After the catalytic reaction, the reaction mixture was collected, the insoluble catalyst was recovered by simple filtration technique, and the product was determined by gas chromatography. GC analysis showed conversion was about 99.3% and selectivity of the m-chloroaniline was 99.9%.

Example 11

1 mmol (157.5 mg) of p-chloronitrobenzene was dissolved in ethyl acetate (5 ml) and 16 mg of catalyst containing $Pt^0$-nanoparticles supported on modified montmorillonite clay reduced by $NaBH_4$ was added in a 50 ml hastelloy autoclave equipped with temperature and pressure control. The reaction vessel was purged with $H_2$ gas for about 5 min and then pressurized with $H_2$ gas up to 20 bar at room temperature (25° C.). The reaction was carried out at temperature 45° C. for a period of 15 min at 500 rpm. After the catalytic reaction, the reaction mixture was collected, the insoluble catalyst was recovered by simple filtration technique, and the product was determined by gas chromatography. GC analysis showed conversion was about 97.8% and selectivity of the p-chloroaniline was 97.5%.

Example 12

1 mmol (157.5 mg) of chloronitrobenzene (ortho and para) was dissolved in ethyl acetate (5 ml) and 16 mg of catalyst containing $Pt^0$-nanoparticles supported on modified montmorillonite clay reduced by hydrazine was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 15 min at 500 rpm. After the catalytic reaction, the reaction mixture was collected, the insoluble catalyst was recovered by simple filtration technique, and the product was determined by gas chromatography. GC analysis showed conversion of o-chlorobenzene was about 100% and selectivity of the o-chloroaniline was 99.6% and conversion of p-chlorobenzene was about 99.6% and selectivity of the p-chloroaniline was 98.3%.

Example 13

1 mmol (157.5 mg) of m-chloronitrobenzene was dissolved in ethyl acetate (5 ml) and 16 mg of catalyst containing $Pt^0$-nanoparticles supported on modified montmorillonite clay reduced by hydrazine was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 30 min at 500 rpm. After the catalytic reaction, the reaction mixture was collected, the insoluble catalyst was recovered by simple filtration technique, and the product was determined by gas chromatography. GC analysis showed conversion was about 98.9% and selectivity of the m-chloroaniline was 99.7%.

Example 14

1 mmol (157.5 mg) of chloronitrobenzene (ortho and para) was dissolved in ethyl acetate (5 ml) and 16 mg of catalyst containing $Pt^0$-nanoparticles supported on modified montmorillonite clay reduced by ethylene glycol was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 15 min at 500 rpm. After the catalytic reaction, the reaction mixture was collected, the insoluble catalyst was recovered by simple filtration technique, and the product was determined by gas chromatography. GC analysis showed conversion of o-chlorobenzene was about 99.7% and selectivity of the o-chloroaniline was 99.9% and conversion of p-chlorobenzene was about 98.0% and selectivity of the p-chloroaniline was 98.5%.

Example 15

1 mmol (157.5 mg) of m-chloronitrobenzene was dissolved in ethyl acetate (5 ml) and 16 mg of catalyst containing $Pt^0$-nanoparticles supported on modified montmorillonite clay reduced by ethylene glycol was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 30 min at 500 rpm. After the catalytic reaction, the reaction mixture was collected, the insoluble catalyst was recovered by simple filtration technique, and the product was determined by gas chromatography. GC analysis showed conversion was about 99.9% and selectivity of the m-chloroaniline was 95.3%.

Example 16

1 mmol (157.5 mg) of chloronitrobenzene (ortho and para) was dissolved in ethyl acetate (5 ml) and added 16 mg of catalyst containing $Pt^0$-nanoparticles supported on modified montmorillonite clay reduced by hydrogen gas in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 15 min at 500 rpm. After the catalytic reaction, the reaction mixture was collected, the insoluble catalyst was recovered by simple filtration technique, and the product was determined by gas chromatography. GC analysis showed conversion of o-chlorobenzene was about 99.7% and selectivity of the o-chloroaniline was 99.7% and conversion of p-chlorobenzene was about 96.0% and selectivity of the p-chloroaniline was 100%.

Example 17

1 mmol (157.5 mg) of m-chloronitrobenzene was dissolved in ethyl acetate (5 ml) and 16 mg of catalyst containing $Pt^0$-nanoparticles supported on modified montmorillonite clay reduced by hydrogen gas was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 30 min at 500 rpm. After the catalytic reaction, the reaction mixture was collected, the insoluble catalyst was recovered by simple filtration technique, and the product was determined by gas chromatography. GC analysis showed conversion was about 100.0% and selectivity of the m-chloroaniline was 99.6%.

Example 18

1 mmol (157.5 mg) of chloronitrobenzene (ortho and para) was dissolved in ethyl acetate (5 ml) and 16 mg of catalyst containing $Pt^0$-nanoparticles supported on modified montmorillonite clay reduced by sodium citrate was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 60 min at 500 rpm. After the catalytic reaction, the reaction mixture was collected, the insoluble catalyst was recovered by simple filtration technique, and the product was determined by gas chromatography. GC analysis showed conversion of o-chlorobenzene was about 99.9% and selectivity of the o-chloroaniline was 99.5% and conversion of p-chlorobenzene was about 98.2% and selectivity of the p-chloroaniline was 97.8%.

Example 19

1 mmol (157.5 mg) of m-chloronitrobenzene was dissolved in ethyl acetate (5 ml) and 16 mg of catalyst containing $Pt^0$-nanoparticles supported on modified montmorillonite clay reduced by sodium citrate was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 90 min at 500 rpm. After the catalytic reaction, the reaction mixture was collected, the insoluble catalyst was recovered by simple filtration technique, and the product was determined by gas chromatography. GC analysis showed conversion was about 99.9% and selectivity of the m-chloroaniline was 99.7%.

Example 20

1 mmol (157.5 mg) of m-chloronitrobenzene was dissolved in ethyl acetate (5 ml) and 11.2 mg of recycled catalyst containing $Pt^0$-nanoparticles supported on modified montmorillonite clay reduced by hydrogen gas was added in a 50 ml hastelloy autoclave equipped with temperature and pressure control. The reaction vessel was purged with $H_2$ gas for about 5 min and then pressurized with $H_2$ gas up to 10 bar at room temperature (25° C.). The reaction was carried out at temperature 45° C. for a period of 15 min at 500 rpm. After the catalytic reaction, the reaction mixture was collected, the insoluble catalyst was recovered by simple filtration technique, and the product was determined by gas chromatography. GC analysis showed conversion was about 92.9% and selectivity of the m-chloroaniline was 99.9%.

One main advantage of the embodiments of the present invention includes providing a novel and eco-friendly process for generation of $Pt^0$-nanoparticles. Another main advantage of the embodiments of the present invention is that the montmorillonite is easily modified by activation with mineral acids under controlled condition for generating desired nanopores 0-8 nm. Additionaly, a main advantage of the embodiments of the present invention is the $Pt^0$-nanoparticles (0-8 nm) generated into the nanopores of the modified montmorillonite clay are very stable and robust. Further, another main advantage of the embodiments of the present invention is that the hydrogenation reaction can be carried out at a temperature 45° C. and pressure 5-20 bar. The embodiments of the present invention are distinguished from the prior art in that the process can yield high selectivity (>99%) with conversion up to 100% within a period of about 15 min. Further, the embodiments of the present invention utilize a clean and inexpensive clay based solid support for generation of $Pt^0$-nanoparticles in the size range 0-10 nm into the nanopores of the acid activated modified montmorillonite clay. Additionally, the embodiments of the present invention utilize a reusable catalyst with good activity. Another main advantage of the embodiments of the present invention is that separation of the catalyst from the reaction mixture is easy.

The invention claimed is:

1. A process for reducing chloronitrobenzene catalyzed by platinum-nanoparticles stabilized on modified montmorillonite clay wherein the said process comprises the steps of:
   a) dissolving chloronitrobenzene in ethyl acetate in the mole ratio of 1:50 to obtain a solution;
   b) adding $Pt^0$-nanoparticles stabilized on modified montmorillonite as catalyst in the mole ratio of 1:82 with respect to chloronitrobenzene to the solution obtained in step a to obtain a reaction mixture;
   c) purging $H_2$ gas for 5 min in the reaction mixture obtained in step b and then pressurizing with $H_2$ gas with a pressure in the range of 5 bar to 20 bar at room temperature; and
   d) heating the reaction mixture as obtained in step c to a temperature in the range of 40° C. to 50° C. for a period in the range of 5 minutes to 240 minutes at 500 rpm to obtain chloroaniline.

2. The process according to claim 1, wherein the pressure is preferably 10 bar.

3. The process according to claim 1, wherein the period of reaction is preferably in the range of 15 minutes to 30 minutes.

4. The process according to claim 1, wherein the temperature of step (d) is preferably 45° C.

5. The process according to claim 1, wherein the chloronitrobenzene is reduced to chloroaniline at a conversion rate up to 100% and a selectivity rate up to 100%.

* * * * *